US009005682B2

(12) United States Patent
Sprenger et al.

(10) Patent No.: US 9,005,682 B2
(45) Date of Patent: Apr. 14, 2015

(54) SYNBIOTIC MIXTURE

(75) Inventors: Norbert Sprenger, Savigny (CH); Francois Morgan, Rennes (FR); Rafael Berrocal, Saint-Legier (CH); Marcel Braun, Konolfingen (CH); Christine Cherbut, Pully (CH); Peter Duncan, Epalinges (CH)

(73) Assignee: Nestec S.A., Vevey (CH)

( * ) Notice: Subject to any disclaimer, the term of this patent is extended or adjusted under 35 U.S.C. 154(b) by 1903 days.

(21) Appl. No.: 12/281,448

(22) PCT Filed: Mar. 7, 2007

(86) PCT No.: PCT/EP2007/001961
§ 371 (c)(1),
(2), (4) Date: Oct. 16, 2008

(87) PCT Pub. No.: WO2007/101675
PCT Pub. Date: Sep. 13, 2007

(65) Prior Publication Data
US 2009/0041736 A1 Feb. 12, 2009

(30) Foreign Application Priority Data
Mar. 7, 2006 (EP) .................................. 06110805

(51) Int. Cl.
| A23L 1/308 | (2006.01) |
| A23L 1/0528 | (2006.01) |
| A23C 9/123 | (2006.01) |
| A01N 63/02 | (2006.01) |
| A23C 9/142 | (2006.01) |
| A23L 1/29 | (2006.01) |
| A23L 1/30 | (2006.01) |
| A61K 47/26 | (2006.01) |
| A01N 63/00 | (2006.01) |

(52) U.S. Cl.
CPC ............. *A61K 35/747* (2013.01); *A23C 9/1425* (2013.01); *A23L 1/296* (2013.01); *A23L 1/30* (2013.01); *A23L 1/3014* (2013.01); *A23V 2002/00* (2013.01); *A23Y 2220/73* (2013.01); *A23Y 2300/55* (2013.01); *A61K 35/745* (2013.01); *A61K 47/26* (2013.01)

(58) Field of Classification Search
USPC .................................. 424/93.4, 93.45; 426/61
See application file for complete search history.

(56) References Cited

U.S. PATENT DOCUMENTS

| 5,494,664 A | 2/1996 | Brassart et al. |
| 5,603,930 A | 2/1997 | Brassart et al. |
| 5,895,648 A | 4/1999 | Cavaliere Vesely et al. |
| 2003/0060445 A1 | 3/2003 | Wilson |
| 2003/0129278 A1 | 7/2003 | Stahl et al. |
| 2004/0072794 A1 | 4/2004 | Kaup et al. |
| 2009/0238774 A1* | 9/2009 | Connolly et al. ............... 424/48 |
| 2010/0086527 A1* | 4/2010 | Huber-Haag et al. ...... 424/93.45 |

FOREIGN PATENT DOCUMENTS

| CA | 2500724 | 6/2005 |
| CA | 2532062 | 7/2006 |
| EP | 0199535 | 4/1986 |
| EP | 0577903 | 1/1994 |
| EP | 0768375 | 4/1997 |
| EP | 904784 | 3/1999 |
| EP | 1243273 | 9/2002 |
| EP | 1384483 | 1/2004 |
| EP | 1629850 | 3/2006 |
| WO | 9700078 | 1/1997 |
| WO | 0053200 | 9/2000 |
| WO | 02060276 | 8/2002 |
| WO | 2004041291 | 5/2004 |
| WO | 2005000748 | 1/2005 |
| WO | 2005039319 | 5/2005 |
| WO | 2006087391 | 8/2006 |

OTHER PUBLICATIONS

Barile et al. (2009) Permeate from cheese whey ultrafiltration is a source of milk oligosaccharides. International Dairy Journal 19: 524-530.*
Foda et al. (2000) Continuous production of oligosaccharides from whey using a membrane reactor. Process Biochemistry 35: 581-587.*
Gopal and Gill (2000) Oligosaccharides and glycoconjugates in bovine milk and colostrum. British Journal of Nutrition 84(Suppl. 1): S69-S74.*
Stanciu et al. (2005) Using the permeate from whey ultrafiltration to obtain synbiotic products for human and animal use. The Annals of the University Dunarea de Jos of Galati 2: 57-62.*
Fanaro S et al, entitled "Acidic Oligosaccharides From Pectin Hydrolysate As New Component for Infant Formulae: Effect on Intestinal Flora, Stool Characteristics, and Ph", Journal of Pediatric Gastroenterology and Nutrition, Aug. 2005, vol. 41, No. 2, pp. 186-190.
Gunasekera Hasantha, entitled "Designer Infant Formulas; Making a Killing", Journal of the Royal Society of Medicine, 2005, vol. 98, No. 12, pp. 551-552.

(Continued)

*Primary Examiner* — Jon P Weber
*Assistant Examiner* — Kailash C Srivastava
(74) *Attorney, Agent, or Firm* — K&L Gates LLP

(57) ABSTRACT

This invention relates to a preparation comprising a probiotic bacterial strain and a prebiotic mixture comprising 5-70 wt % of at least one N-acetylated oligosaccharide selected from the group comprising GalNAcα1,3Galβ1,4Glc and Galβ1,6GalNAcα1,3Galβ1,4Glc, 20-95 wt % of at least one neutral oligosaccharide selected from the group comprising Galβ1,6Gal, Galβ1,6Galβ1,4Glc Galβ1,6Galβ1,6Glc, Galβ1,3Galβ1,3Glc, Galβ1,3Galβ1,4Glc, Galβ 1,6Galβ 1,6Galβ 1,4Glc, Galβ 1,6Galβ 1,3Galβ 1,4Glc Galβ 1,3Galβ 1,6Galβ 1,4Glc and Galβ1,3Galβ1,3Galβ1,4Glc and 2-50 wt % of at least one sialylated oligosaccharide selected from the group comprising NeuAcα2,3Galβ1,4Glc and NeuAcα2,6Galβ1,4Glc. The invention extends to food products comprising said preparation and to the use of the preparation in the prevention and treatment of infections.

15 Claims, 6 Drawing Sheets

(56) References Cited

OTHER PUBLICATIONS

Haschke F et al, entitled "Clinical Trials Prove the Safety and Efficacy of the Probiotic Strain *Bifidobacterium* Bb12 in Follow-Up Formula and Growing-Up Milks", 1998, vol. 146, No. 8, SUPPL 1, pp. S26-S30.

Kunz C et al, entitled "Biological Functions of Oligsaccharides in Human Milk", 1993, vol. 82, No. 11, pp. 903-912.

Martin R et al, entitled "The Commensal Microflora of Human Milk: New Perspectives for Food Bacteriotherapy and Probiotics", 2003, pp. 121-127.

Martin R et al, entitled "Probiotic Potential of 3 *Lactobacilli* Strains Isolated From Breast Milk", 2005, vol. 21, No. 1, pp. 8-17.

Thurl Stephan et al, entitled "Quantification of Individual Oligosaccharide Compounds From Human Milk Using High-ph Anion-Exchange Chromatography", 1996, vol. 235, No. 2, pp. 202-206.

Martin Rocio et al., entitled "Probiotic potential of 3 *Lactobacilli* strains isolated from breast milk", Journal of Human Lactation: Official Journal of International Lactation Consultant Association, 2005, vol. 21, No. 1, pp. 8-17.

Glenn R. Gibson et al., "Dietary Modulation of the Human Colonic Microbiota: Introducing the Concept of Prebiotics", The Journal of Nutrition, vol. 25, No. 6, Jun. 1995, pp. 1401-1412.

Katja Hatakka, entitled "Effect of Long Term Consumption of Probiotic Milk on Infections in Children Attending Day Care Centres: Double Blind, Randomised Trial", 2001, BMJ, vol. 322, pp. 1-5.

International Search Report dated Jul. 11, 2007, 6 pages.
Written Opinion dated Jul. 11, 2007, 15 pages.

\* cited by examiner

Data shown represent the mean +/- SEM. * p<0.05 (t test) vs cumulative protection given by bacteria alone + 3SL alone

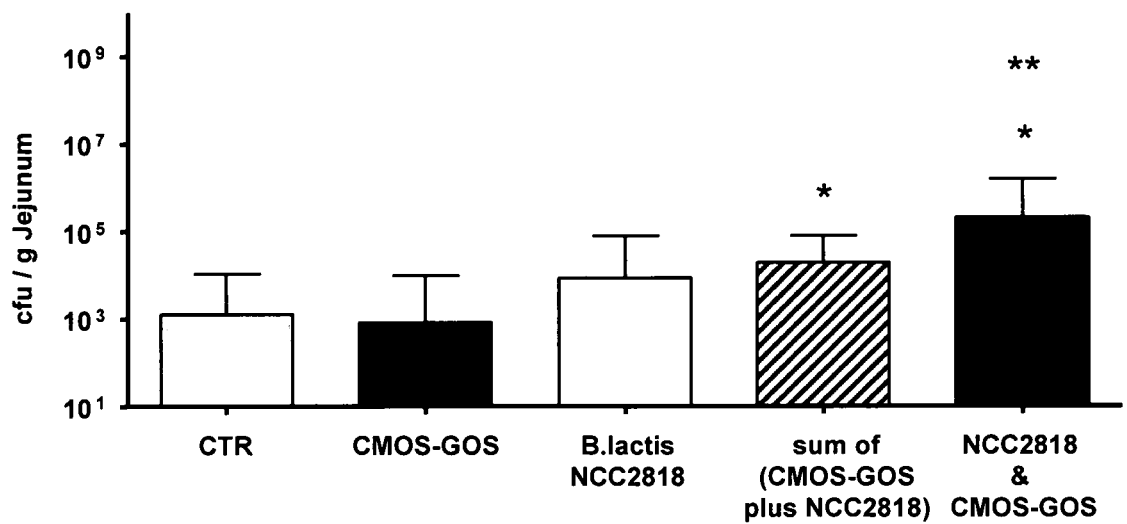
Figure 3. *B. breve* counts in small intestine (jejunum) after 2 weeks treatment with prebiotic mixture (CMOS-GOS) in diet and Bifidobacterium lactis CNCM I-3446 (NCC 2818) in water. Significance by unpaired t-test (p<0.05): * significant difference to control group (CTR); ** significant difference to sum of prebiotic mixture plus probiotic

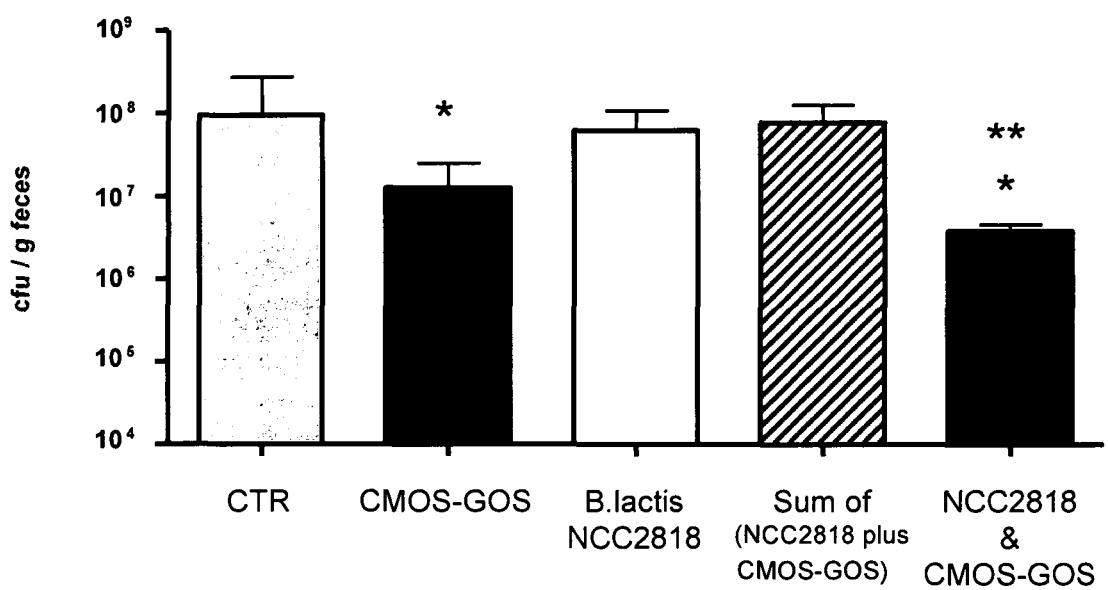
Figure 4. *Staphylococci* counts in faeces after 2 weeks treatment with prebiotic mixture (CMOS-GOS) in diet and Bifidobacterium lactis CNCM I-3446 (NCC 2818) in water. Significance by unpaired t-test ($p<0.05$): * significant difference to control group (CTR); ** significant difference to sum of prebiotic mixture plus probiotic.

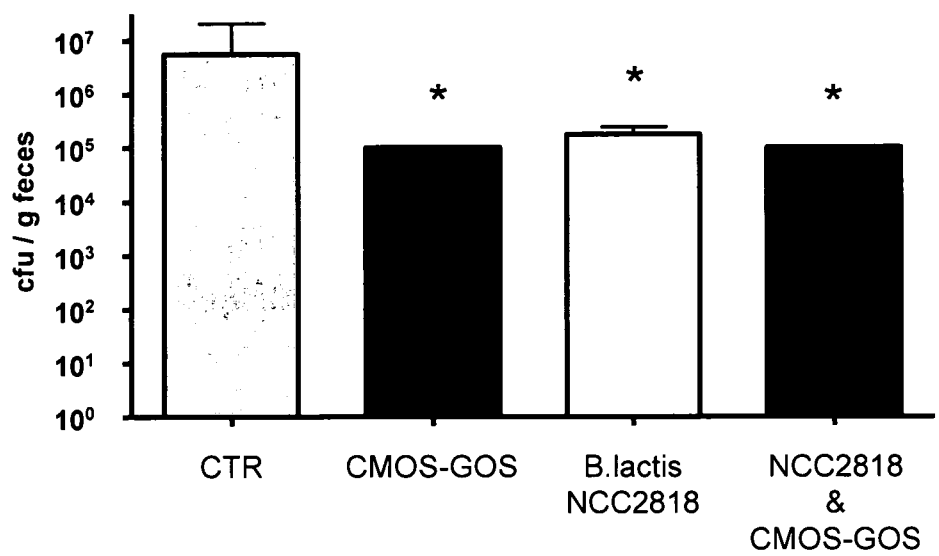
Figure 5. *Clostridium perfringens* counts in feces after 2 weeks treatment with prebiotic mixture (CMOS-GOS) in diet and Bifidobacterium l

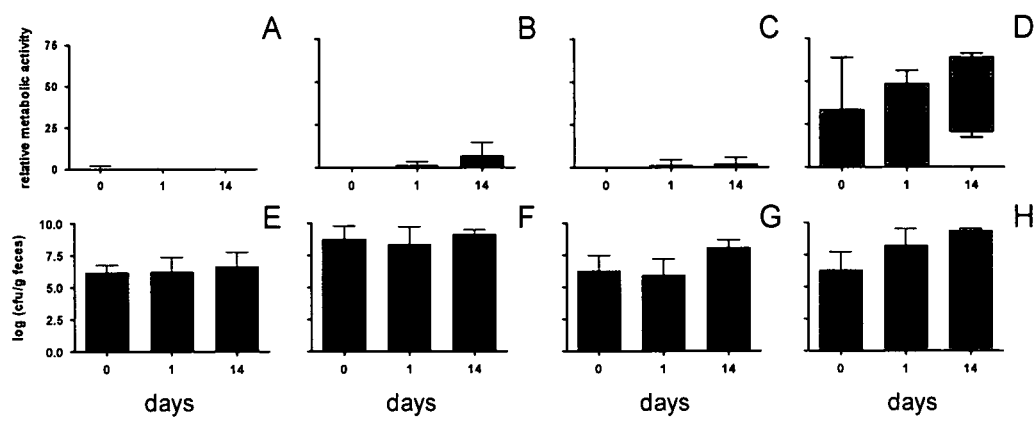

Figure 6. Relative metabolic activity with median and interquartile range (A,B,C,D) and means with standard deviation (E,F,G,H) of resident *B. longum* over time of microbiota establishment. Represented are control group (A,E; ■), group with prebiotic mixture (B,F; ■), group with *Lactobacillus rhamnosus* CGMCC 1.3724 (NCC 4007) (C,G; ■), and group with preparation according to the invention (D,H; ■). (N = 9 to 10)

SYNBIOTIC MIXTURE

FIELD OF THE INVENTION

This invention relates to preparations comprising a probiotic and a prebiotic mixture which is specifically designed to enhance the efficiency and the efficacy of the probiotic and to food products comprising said preparation.

BACKGROUND OF THE INVENTION

The human colon is colonised with a wide range of bacteria that have both positive and negative effects on gut physiology as well as having other systemic influences. Predominant groups of bacteria found in the colon include *bacteroides, bifidobacteria, eubacteria, clostridia* and *lactobacilli*. The bacteria present have fluctuating activities in response to substrate availability, redox potential, pH, $O_2$ tension and distribution in the colon. In general intestinal bacteria can be divided into species that may potentially exert either harmful or beneficial effects on the host. Pathogenic effects (which may be caused by *clostridia* or *bacteroides*, for example) include diarrhoea, infections, liver damage, carcinogenesis and intestinal putrefaction. Health-promoting effects may be caused by the inhibition of growth of, and colonisation by, harmful bacteria, stimulation of immune functions, improving digestion and absorption of essential nutrients and synthesis of vitamins. An increase in the numbers and/or activities of bacterial species such as *Bifidobacterium* and *Lactobacillus* that may have health promoting properties is desirable.

In the recent past, certain strains of bacteria have attracted considerable attention because they have been found to exhibit valuable properties for man if ingested. In particular, specific strains of the genera *Lactobacilli* and *Bifidobacteria* have been found to be able to colonise at least transiently the intestinal mucosa, to reduce the capability of pathogenic bacteria to adhere to the intestinal epithelium, to have immunomodulatory effects and to assist in the maintenance of well-being. Such bacteria are commonly called probiotics.

Extensive studies have been carried out to identify new probiotic strains. For example, EP 0 199 535, EP 0 768 375, WO 97/00078, EP 0 577 903 and WO 00/53200 disclose specific strains of *lactobacilli* and *bifidobacteria* and their beneficial effects.

A probiotic may be defined as a live microbial feed supplement which beneficially affects the host animal by improving its intestinal microbial balance. Certain strains of *Lactobacilli* and *Bifidobacteria* such as, for example, *Lactobacillus paracasei* CNCM I-2116, *Lactobacillus rhamnosus* ATCC 53103, *Bifidobacterium lactis* BB12®, *Bifidobacterium longum* ATCC BAA-999 *Lactobacillus reuteri* ATCC 55730 and *Bifidobacterium breve* M-16V® have been demonstrated to have these properties. Such probiotic *lactobacilli* and *bifidobacteria* are commonly added to human foods, such as fermented milk products. It is known that probiotics generally have a prophylactic and therapeutic effect on pathogenic infections of the gastrointestinal tract such as those caused by *Clostridia* and *Salmonella* species for example. In EP 904 784 it is proposed to use a combination of three different types of probiotic for the treatment of gastrointestinal disorders. More recently, it has been suggested that some probiotic strains may also be effective in the prevention and treatment of infections of the upper respiratory tract (British Medical Journal 2001, 322:1-5).

As far as infants specifically are concerned, immediately before birth, the gastrointestinal tract of a baby is thought to be sterile. During the process of birth, it encounters bacteria from the digestive tract and skin of the mother and starts to become colonised. Large differences exist with respect to the composition of the gut microbiota in response to the infant's feeding. The faecal flora of breast-fed infants includes appreciable populations of *bifidobacteria* with some *lactobacilli*, whereas formula-fed infants have more complex microbiota, with *bifidobacteria, bacteroides, clostridia* and *streptococci* all usually present. After weaning, a pattern of gut microbiota that resembles the adult pattern becomes established.

Mother's milk is recommended for all infants. However, in some cases breast feeding is inadequate or unsuccessful for medical reasons or the mother chooses not to breast feed. Infant formulae have been developed for these situations.

It has been proposed to add probiotics to infant formulae to encourage gut colonization to take place and to promote colonization with the "good" bacteria—*bifidobacteria* and *lactobacilli*—rather than the harmful bacteria—pathogens such as *clostridia*, etc. Typically a minimum of $10^7$ cfu/g of formula is added although generally larger amounts are preferred, for example up to $10^{12}$ cfu/g of formula.

Another approach to promote the numbers and/or activities of beneficial bacteria in the colon is the addition of prebiotics to foodstuffs. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS).

Human milk is known to contain a larger amount of indigestible oligosaccharides than most other animal milks. In fact, indigestible oligosaccharides represent the third largest solid component (after lactose and lipids) in breast milk, occurring at a concentration of 12-15 g/l in colostrum and 5-8 g/l in mature milk. Human milk oligosaccharides are very resistant to enzymatic hydrolysis, indicating that these oligosaccharides may display essential functions not directly related to their calorific value.

As the composition of human milk becomes better understood, it has also been proposed to add prebiotics to infant formula. Various infant formulas supplemented with prebiotics such as mixtures of fructooligosaccharides and galactooligosaccharides for example are commercially available. However, such mixtures approximate only roughly the mixture of oligosaccharides in human milk. Over 100 different oligosaccharide components have been detected in human milk some of which have not been so far detected in animal milks such as bovine milk at all or have been detected only in small quantities. Examples of classes of human milk oligosaccharide that are present in bovine milk and colostrum only in very small quantities or not at all are sialylated and fucosylated oligosaccharides.

Infant formulas containing both probiotics and prebiotics have also been proposed in the continual quest to produce infant formulas which replicate as closely as possible the composition and efficacy of human milk. For example, in WO 2005/000748 it is proposed to supplement infant formula with a mixture of a *Bifidobacterium breve* strain, galactooligosaccharides and fructooligosaccharides (inulin). It is claimed that this mixture, which is described as a synbiotic, regulates the *Bifidobacterium* population in the colon of infants which consume the supplemented formula to a more "infant-like" population, that is, lower in *Bifidobacterium*

*catenulatum, Bifidobacterium pseudocatenulatum* and *Bifidobacterium adolescentis* species and higher in *Bifidobacterium infantis, Bifidobacterium breve* and *Bifidobacterium longum* species. The mixture is also stated to be useful for the prevention or treatment of an immune condition.

However, a need remains for preparations comprising a probiotic and a prebiotic mixture specifically designed to enhance the efficiency and the efficacy of the probiotic.

SUMMARY OF THE INVENTION

It has now surprisingly been found that a prebiotic mixture which comprises 5-70 wt % of at least one N-acetylated oligosaccharide selected from the group comprising GalNAcα1,3Galβ1,4Glc and Galβ1,6GalNAcα1, 3Galβ1,4Glc, 20-90 wt % of at least one neutral oligosaccharide selected from the group comprising Galβ1,6Gal, Galβ1,6Galβ1,4Glc Galβ1,6Galβ1,6Glc, Galβ1, 3Galβ1,3Glc, Galβ1,3Galβ1,4Glc, Galβ1,6Galβ1, 6Galβ1,4Glc, Galβ1,6Galβ1,3Galβ1,4Glc Galβ1, 3Galβ1,6Galβ1,4Glc and Galβ1,3Galβ1,3Galβ1,4Glc and 5-50 wt % of at least one sialylated oligosaccharide selected from the group comprising NeuAcα2,3Galβ1,4Glc and NeuAcα2,6Galβ1,4Glc is highly efficacious in enhancing the beneficial effects and efficiency of probiotic bacteria co-administered with the prebiotic mixture.

Accordingly, in a first aspect, the present invention provides a preparation comprising a probiotic bacterial strain and a prebiotic mixture comprising 5-70 wt % of at least one N-acetylated oligosaccharide selected from the group comprising GalNAcα1,3Galβ1,4Glc and Galβ1,6GalNAcα1, 3Galβ1,4Glc, 20-95 wt % of at least one neutral oligosaccharide selected from the group comprising Galβ1,6Gal, Galβ1,6Galβ1,4Glc Galβ1,6Galβ1,6Glc, Galβ1, 3Galβ1,3Glc, Galβ1,3Galβ1,4Glc, Galβ1,6Galβ1, 6Galβ1,4Glc, Galβ1,6Galβ1,3Galβ1,4Glc Galβ1, 3Galβ1,6Galβ1,4Glc and Galβ1,3Galβ1,3Galβ1,4Glc and 2-50 wt % of at least one sialylated oligosaccharide selected from the group comprising NeuAcα2,3Galβ1,4Glc and NeuAcα2,6Galβ1,4Glc.

In a second aspect, the present invention provides the use of a probiotic bacterial strain and a prebiotic mixture comprising 5-70 wt % of at least one N-acetylated oligosaccharide selected from the group comprising GalNAcα1,3Galβ1, 4Glc and Galβ1,6GalNAcα1,3Galβ1,4Glc, 20-95 wt % of at least one neutral oligosaccharide selected from the group comprising Galβ1,6Gal, Galβ1,6Galβ1,4Glc Galβ1, 6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1, 4Glc Galβ1,3Galβ1,6Galβ1,4Glc and Galβ1,3Galβ1, 3Galβ1,4Glc and 2-50 wt % of at least one sialylated oligosaccharide selected from the group comprising NeuAcα2, 3Galβ1,4Glc and NeuAcα2,6Galβ1,4Glc in the manufacture of a medicament for the prevention and/or treatment of pathogenic infections of the gastro-intestinal tract.

In a third aspect, the present invention provides the use of a probiotic bacterial strain and a prebiotic mixture comprising 5-70 wt % of at least one N-acetylated oligosaccharide selected from the group comprising GalNAcα1,3Galβ1, 4Glc and Galβ1,6GalNAcα1,3Galβ1,4Glc, 20-95 wt % of at least one neutral oligosaccharide selected from the group comprising Galβ1,6Gal, Galβ1,6Galβ1,4Glc Galβ1, 6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1, 4Glc Galβ1,3Gaβ1,6Galβ1,4Glc and Galβ1,3Galβ1, 3Galβ1,4Glc and 2-50 wt % of at least one sialylated oligosaccharide selected from the group comprising NeuAcα2, 3Galβ1,4Glc and NeuAcα2,6Galβ1,4Glc in the manufacture of a medicament for the prevention or treatment of an immune condition.

In a fourth aspect, the present invention provides the use of a probiotic bacterial strain and a prebiotic mixture comprising 5-70 wt % of at least one N-acetylated oligosaccharide selected from the group comprising GalNAcα1,3Galβ1, 4Glc and Galβ1,6GalNAcα1,3Galβ1,4Glc, 20-95 wt % of at least one neutral oligosaccharide selected from the group comprising Galβ1,6Gal, Galβ1,6Galβ1,4Glc Galβ1, 6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1, 4Glc Galβ1,3Galβ1,6Galβ1,4Glc and Galβ1,3Galβ1, 3Galβ1,4Glc and 2-50 wt % of at least one sialylated oligosaccharide selected from the group comprising NeuAcα2, 3Galβ1,4Glc and NeuAcα2,6Galβ1,4Glc in the manufacture of a medicament for the prevention or treatment of infections of the upper respiratory tract.

In a fifth aspect, the invention provides a method for the prevention or treatment of pathogenic infections of the gastro-intestinal tract in a subject in need thereof which comprises administering to the subject a therapeutic amount of a preparation comprising a probiotic bacterial strain and a prebiotic mixture comprising 5-70 wt % of at least one N-acetylated oligosaccharide selected from the group comprising GalNAcα1,3Galβ1,4Glc and Galβ1,6GalNAcα1, 3Galβ1,4Glc, 20-95 wt % of at least one neutral oligosaccharide selected from the group comprising Galβ1,6Gal, Galβ1,6Galβ1,4Glc Galβ1,6Galβ1,6Glc, Galβ1, 3Galβ1,3Glc, Galβ1,3Galβ1,4Glc, Galβ1,6Galβ1, 6Galβ1,4Glc, Galβ1,6Galβ1,3Galβ1,4Glc Galβ1, 3Galβ1,6Galβ1,4Glc and Gaβ1,3Galβ1,3Galβ1,4Glc and 2-50 wt % of at least one sialylated oligosaccharide selected from the group comprising NeuAcα2,3Galβ1,4Glc and NeuAcα2,6Galβ1,4Glc.

In a sixth aspect, the invention provides a method for the prevention or treatment of an immune condition in a subject in need thereof which comprises administering to the subject a therapeutic amount of a preparation comprising a probiotic bacterial strain and a prebiotic mixture comprising 5-70 wt % of at least one N-acetylated oligosaccharide selected from the group comprising GalNAcα1,3Galβ1,4Glc and Galβ1, 6GalNAcα1,3Galβ1,4Glc, 20-95 wt % of at least one neutral oligosaccharide selected from the group comprising Galβ1,6Gal, Galβ1,6Galβ1,4Glc Galβ1,6Galβ1,6Glc, Galβ1,3Galβ1,3Glc, Galβ1,3Galβ1,4Glc, Galβ1, 6Galβ1,6Galβ1,4Glc, Galβ1,6Galβ1,3Galβ1,4Glc Galβ1,3Galβ1,6Galβ1,4Glc and Galβ1,3Galβ1,3Galβ1, 4Glc and 2-50 wt % of at least one sialylated oligosaccharide selected from the group comprising NeuAcα2,3Galβ1,4Glc and NeuAcα2,6Galβ1,4Glc.

In a seventh aspect, the invention provides a method for the prevention or treatment of an upper respiratory tract infection in a subject in need thereof which comprises administering to the subject a therapeutic amount of a preparation comprising a probiotic bacterial strain and a prebiotic mixture comprising 5-70 wt % of at least one N-acetylated oligosaccharide selected from the group comprising GalNAcα1,3Galβ1, 4Glc and Galβ1,6GalNAcα1,3Galβ1,4Glc, 20-95 wt % of at least one neutral oligosaccharide selected from the group comprising Galβ1,6Gal, Galβ1,6Galβ1,4Glc Galβ1, 6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1, 4Glc Galβ1,3Galβ1,6Galβ1,4Glc and Galβ1,3Galβ1, 3Galβ1,4Glc and 2-50 wt % of at least one sialylated oligosaccharide selected from the group comprising NeuAcα2, 3Galβ1,4Glc and NeuAcα2,6Galβ1,4Glc.

BRIEF DESCRIPTION OF THE DRAWINGS

FIG. 3 compares the *Bifidobacterium breve* counts in the small intestine of gnotobiotic mice gavaged with a human infant microbiota and fed the preparation of the invention with the *Bifidobacterium breve* counts in mice fed the components of the preparation alone;

FIG. 4 compares the *Staphylococci* counts in the faeces of gnotobiotic mice gavaged with a human infant microbiota and fed the preparation of the invention with the *Staphylococci* counts in mice fed the components of the preparation alone;

FIG. 5 compares the *Clostridium perfringens* counts in the small intestine of gnotobiotic mice gavaged with a human infant microbiota and fed the preparation of the invention with the *Clostridium perfringens* counts in such mice fed the components of the preparation alone; and FIG. 6 compares the relative metabolic activity of resident *Bifidobacterium longum* over a period of two weeks in germ-free mice gavaged with a human infant microbiota and fed the preparation of the invention with the relative metabolic activity of resident *Bifidobacterium longum* in such mice fed the components of the preparation alone

DETAILED DESCRIPTION OF THE INVENTION

Figure 1:
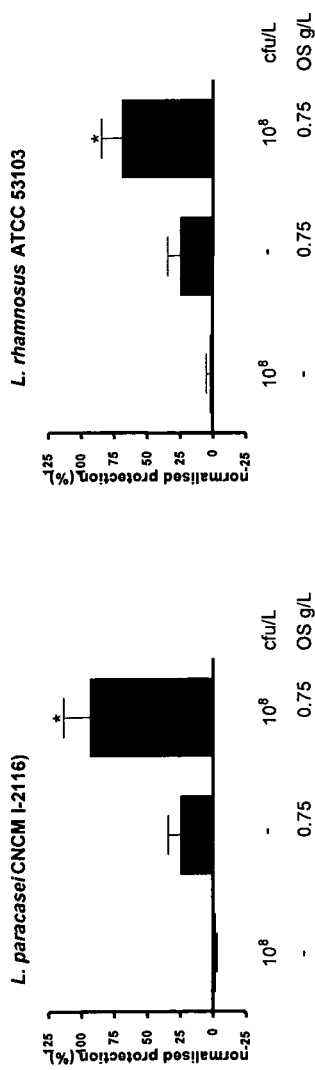
FIG. 1 shows the protective effect of the preparation of the invention against toxin A from *Clostridium difficile* compared with the protective effect given by the components of the preparation alone.

In the present specification, the following words are given a definition that must be taken into account when reading and interpreting the description, examples and claims:

"bifidogenic intestinal microbiota" means for infants an intestinal microbiota which is dominated by *Bifidobacteria* such as *Bifidobacterium breve, Bifidobacterium infantis*, and *Bifidobacterium longum* to the exclusion of appreciable populations of such species as *Bacteroides, Clostridia* and *Streptococci* and which is generally comparable with that found in breast fed infants;

"infant" means a child under the age of 12 months;

"infant formula" means a foodstuff intended for the complete nutrition of infants during the first four to six months of life and as a complement to other foodstuffs up to the age of 12 months;

"N-acetylated oligosaccharide" means an oligosaccharide having an N-acetyl residue;

NCC designates Nestlé Culture Collection

"neutral oligosaccharide" means an oligosaccharide having no charge and no N-acetyl residue;

"probiotic bacteria" means microbial cell preparations or components of microbial cells with a beneficial effect on the health or well-being of the host. (Salminen S, Ouwehand A. Benno Y. et al "Probiotics: how should they be defined" Trend Food Sci. Technol. 1999:10 107-10);

"prebiotic" means a non-digestible food ingredient that beneficially affects the host by selectively stimulating the growth and/or activity of one or a limited number of bacteria in the colon and thus improves host health. (Gibson and Roberfroid "Dietary Modulation of the Human Colonic Microbiota: Introducing the Concept of Prebiotics" J. Nutr 125:1401-1412);

"oligosaccharide" means a carbohydrate having a degree of polymerisation (DP) ranging from 2 to 20 inclusive but not including lactose; and "sialylated oligosaccharide" means an oligosaccharide having a sialic acid residue with associated charge Preferably the prebiotic mixture comprises 10-70 wt % of the N-acetylated oligosaccharides, 20-80 wt % of the neutral oligosaccharides and 10-50 wt % of the sialylated oligosaccharides. More preferably the prebiotic mixture comprises 15-40 wt % of the N-acetylated oligosaccharides, 40-60 wt % of the neutral oligosaccharides and 15-30 wt % of the sialylated oligosaccharides. A particularly preferred prebiotic mixture comprises 30 wt % of the N-acetylated oligosaccharides, 50 wt % of the neutral oligosaccharides and 20 wt % of the sialylated oligosaccharides.

Alternatively, the mixture may conveniently comprise 5-20 wt % of the specified N-acetylated oligosaccharide(s), 60-95 wt % of the specified neutral oligosaccharide(s) and 2-30 wt % of the specified sialylated oligosaccharide(s).

The prebiotic mixture of the invention may be prepared from one or more animal milks. The milk may be obtained from any mammal, in particular from cows, goats, buffalos, horses, elephants, camels or sheep.

Alternatively the prebiotic mixture may be prepared by purchasing and mixing the individual components. For example, synthesised galacto-oligosaccharides such as Gal$\beta$1,6Gal$\beta$1,4Glc Gal$\beta$1,6Gal$\beta$1,6Glc, Gal$\beta$1,3Gal$\beta$1,4Glc, Gal$\beta$1,6Gal$\beta$1,6Gal$\beta$1,4Glc, Gal$\beta$1,6Gal$\beta$1,3Gal$\beta$1,4Glc and Gal$\beta$1,3Gal$\beta$1,6Gal$\beta$1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycosyltransferases, such as galactosyltransferases may be used to produce neutral oligosaccharides.

The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

The sialylated oligosaccharides 3'sialyl-lactose and 6'sialyl-lactose may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

The bacterial strain may be selected from any strain which satisfies the definition of a probiotic and has acceptable shelf-life for the product into which the preparation of the invention is to be incorporated. For example, infant formulae are required to remain stable and effective for up to 36 months. Of course, the preparation of the invention does not need to be incorporated into another product such as a food stuff but may be ingested as is or mixed with a suitable excipient in the form of a powder or capsule or compressed into tablets for example.

The probiotic bacterial strain is preferably a *lactobacillus* or a *bifidobacterium*. Preferably strains which produce only L (+) lactic acid are used. Examples of preferred *Lactobacillus* species are *Lactobacillus rhamnosus, Lactobacillus paracasei* and *Lactobacillus reuteri*. Particularly preferred strains are *Lactobacillus rhamnosus* ATCC 53103, *Lactobacillus rhamnosus* CGMCC 1.3724, *Lactobacillus reuteri* ATCC 55730 and *Lactobacillus paracasei* CNCM I-2116. Examples of preferred *Bifidobacterium* species are *Bifidobacterium lactis, Bifidobacterium breve* and *Bifidobacterium longum*. Particularly preferred strains are the strain of *B. lactis* sold by the Christian Hansen company of Denmark under the trade mark Bb12 and *Bifidobacterium longum* ATCC BAA-999 obtainable from Morinaga Milk Industry Co. Ltd. of Japan under the trade mark BB536.

The preparation of the invention may provide between $10^2$ and $10^{10}$ cfu of probiotic bacteria for each gram of the prebiotic mixture.

In a preferred aspect of the invention, the preparation described above is incorporated into a food product. In the context of the present invention, the term "food product" is intended to encompass any consumable matter. Hence, it may be a product intended for consumption by humans, in particular infant formula, growing up milk, and the like. However, consumption of the preparation is not restricted to infants and children In particular, the preparation of the invention can be incorporated into dehydrated milk or cereal mixtures.

If the preparation of the invention is to be incorporated in infant formula or other milk-based nutritional composition, the composition may be prepared in any suitable manner known in the art. For example, an infant formula may be prepared by blending together the protein source, any carbohydrates other than lactose and the fat source in appropriate proportions. Emulsifiers may be added if desired. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger, e.g. a plate heat exchanger.

The liquid mixture may then be cooled to about 60° C. to about 85° C., for example by flash cooling. The liquid mixture may then be homogenised, for example in two stages at about 7 MPa to about 40 MPa in the first stage and about 2 MPa to about 14 MPa in the second stage. The homogenised mixture may then be further cooled to add any heat sensitive components such as vitamins and minerals. The pH and solids content of the homogenised mixture is conveniently standardised at this point.

The homogenised mixture is transferred to a suitable drying apparatus, such as a spray drier or freeze drier, and converted to powder. The powder should have a moisture content of less than about 5% by weight.

The preparation of the invention may be made up in advance and added directly to nutritional composition by dry mixing. Preferably, however, the individual components of the preparation are added separately to the nutritional composition in which case the prebiotic mixture is preferably added in the liquid phase immediately prior to drying and the probiotic bacterial strain is preferably added to the dried composition by dry mixing.

The selected probiotic bacterial strain may be cultured according to any suitable method known in the art and prepared for addition to the infant formula by freeze-drying or spray-drying for example. Alternatively, bacterial strains can be bought from specialist suppliers such as Christian Hansen and Morinaga already prepared in a suitable form for addition to food products such as infant formula.

If the prebiotic mixture has been prepared from an animal milk, for example as described below, and it is intended to add it to an infant formula, it may be convenient to add it without first removing all the lactose. As infant formula contains a carbohydrate component which is often wholly or partially constituted by lactose, it will be apparent to the person skilled in the art that the amount of carbohydrate in the infant formula will need to be adjusted to take into account the additional carbohydrate that will be added with the prebiotic mixture. The final concentration of the inventive preparation in the baby or infant food product or formula is preferably from 0.3 to 6.0%, preferably 0.75 to 4.0% by weight of dry matter. This corresponds to a concentration of from 0.2 to 8 grams per liter, preferably 1 to 5 g/l of reconstituted formula. However, these amounts should not be considered as limitative and should be adapted to the target population, for example based on the weight and age or health of the baby or infant. Preferably, the formula or feed containing the oligosaccharide mixture of the invention is fed to the baby at every feed.

In addition to the preparation of the invention, a food product such as an infant formula may comprise one or more further oligosaccharides which are added separately up to an oligosaccharide content of 10 g/l of reconstituted or liquid formula.

Although it is preferred to supplement food products specifically targeted towards infant or baby nutrition, it may also be beneficial to supplement food products not specifically targeted, or targeted to the adult population. For example, the oligosaccharide mixtures of the invention can be incorporated into healthcare nutrition products and nutritional products for the elderly. Such food products may include mixes for milk-based drinks, yoghurts, milk-based fermented products, and ice-creams, as well as cereal based products, among others.

Surprisingly, it has been found that the prebiotic mixture in the preparations of the invention synergistically enhances the anti-pathogenic and immunomodulatory properties of the probiotic to produce a therapeutic effect which is markedly superior to the mixture of, for example, the same probiotic with a single prebiotic. The preparations of the invention and food products containing them are thus suitable for the prevention and treatment of gastrointestinal infections caused by pathogens, particularly bacterial pathogens as well as infections of the upper respiratory tract such as otitis media. Food products containing preparations according to the invention are thus especially suitable for vulnerable populations such as babies and the elderly.

Further, the preparations of the invention are suitable for boosting immune defences for example by enhancing response to vaccines and reducing the duration and severity of infections as well as for the prevention and treatment of conditions related to the malfunctioning of the immune system in infants and young children such as food hypersensitivity, eczema, allergic rhinitis, atopic dermatitis and other atopic diseases.

Another advantage of the preparations of the invention is that they promote the establishment of a bifidogenic intestinal microbiota in infants by increasing the relative metabolic activity of the *Bifidobacteria* species which dominate such intestinal microbiota in infants.

The invention will now be illustrated by reference to the following examples.

Example 1

200,000 liters of a whey ultrafiltration permeate are pre-concentrated to 22% (w/w) total solids (TS), pasteurised at about 75° C. for about 30 seconds and then concentrated by evaporation at 60° C. to reach a TS of 59% (w/w). The liquid is cooled in a crystalliser at a rate of 2° C. per hour for a period of 24 hours to crystallise the lactose. Crystallised lactose is washed then removed by a wringer. The remaining liquid is clarified through a decanter. The 77000 liters at 17.7% TS obtained from the clarifier are re-concentrated by evaporation at 60° C. to reach a TS of 55% (w/w) and subject to a second lactose crystallisation step under the same conditions as before. The 29000 liters at 20.5% TS of liquor thereby obtained are demineralised by a combination of electrodialysis and ion exchange in a manner known per se yielding 28500 liters of a 90% demineralised liquor at 17.3% TS. This liquor, which contains approximately 1.5 grams per liter of a mixture of about 30 wt % GalNAcα1,3Galβ1,4Glc and Galβ1,6GalNAcα1,3Galβ1,4Glc, 50 wt % of Galβ1,6Galβ1,4Glc and Galβ1,3Galβ1,4Glc and 20 wt % of NeuAcα2,3Galβ1,4Glc and NeuAcα2,6Galβ1,4Glc, depending upon the starting material, may either be added directly to a food product such as an infant formula or may by further concentrated in a manner known per se to those skilled in the art.

For example, the lactose remaining in the liquor may be hydrolysed into glucose and galactose and these monosaccharides may be either removed by nanofiltration or, if desired, the galactose may be at least partially polymerised for example by the action of β-galactosidase to produce galacto-oligosaccharides which will also be retained by the nanofiltration membrane.

Example 2

100 kg of prebiotic mixture produced according to Example 1 at 50% TS are heated to 60° C. in a standard tank and the pH is adjusted to 6 to 6.5. 4.5 mg of Lactase F (Amano, Japan) are added per gram of TS and the mixture is held at 60° C. for three hours. Then the temperature is raised to 110° C. for 11 seconds by direct steam injection to inactivate the enzyme. The resulting liquid contains approximately 100 grams per liter of a mixture of about 10 wt % GalNAcα1,3Galβ1,4Glc and Galβ1,6GalNAcα1,3Galβ1,4Glc, 87 wt % of Galβ1,6Galβ1,6Glc, Galβ1,6Galβ1,4Glc and Galβ1,3Galβ1,4Glc and 3 wt % of NeuAcα2,3Galβ1,4Glc and NeuAcα2,6Galβ1,4Glc It may either be added directly to a food product such as an infant formula or may be further concentrated as described above.

Example 3

An example of the composition of an infant formula containing a preparation according to the present invention is given below.

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| OS mixture from Example 1 (g) | 1.0 | 6.5 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| *L. rhamnosus* CGMCC 1.3724 | 2.3 × $10^9$ cfu/g of powder | |

Example 4

In vitro experiments were performed to compare the efficacy of preparations according to the invention using two different strains of probiotic bacteria with the efficacy of mixtures of the same probiotic bacteria and other prebiotics in prevention of pathogenic infection. *Clostridium difficile* toxin A was selected as a representative toxin from pathogenic bacteria.

Monolayers of intestinal epithelial T84 cells grown on transwell plates were incubated with (i) a probiotic alone, (ii) a prebiotic alone, or (iii) a combination of probiotic and prebiotic. After a preincubation for 2 hr at 37° C., 5% CO2, T84 cells were challenged with toxin A from *C. difficile* at a concentration of 100 ng/ml. Transepithelial electrical resistance (TER), which served as a marker to assess protection against the action of toxin A, was monitored at regular intervals for up to 24 hr. A normalized protection score was calculated.

The probiotic bacterial strains were *L. paracasei* (CNCM I-2116) and *L. rhamnosus* (ATCC 53103). Both strains were used at final concentrations of $10^8$ cfu/l.

The prebiotics used were the prebiotic mixture described herein at 1 g/l; fructooligosaccharides (Raftilose P95, Orafti, Belgium); galactooligosaccharides (Vivinal GOS, DOMO, The Netherlands) and sialyllactose (Kyowa Hakko Kogyo, Japan) at 10 g/l.

Figure 2:
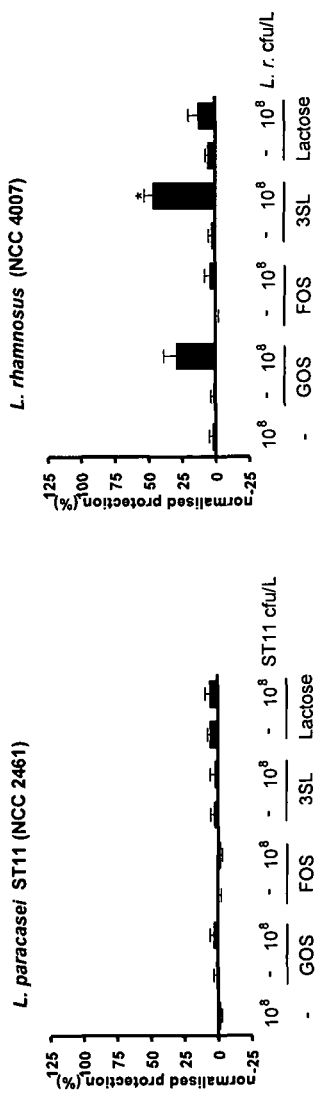
FIG. 2 shows the protective effect against toxin A from *Clostridium difficile* conferred by the probiotic bacterial strains used in FIG. 1 in combination with various different prebiotics known in the art.

The results are shown in FIGS. 1 and 2. FIG. 1 compares the results obtained with the probiotic alone, the prebiotic mixture alone and the preparation of the invention for two probiotic strains. FIG. 2 compares the results obtained with the same probiotic strains as used in FIG. 1 and fructooligosaccharides at 20 g/l; galactooligosaccharides at 20 g/l and sialyllactose at 10 g/l. Lactose (Sigma) at 20 g/l was used as a control.

From FIG. 1, it may be seen that the preparations of the invention had a significant synergistic effect against *C. difficile* toxin A compared with that provided by the individual components (i.e. prebiotic mixture and probiotic strain) alone. From FIG. 2, it may be seen that a comparable effect was not achieved when the same probiotic bacterial strains were tested in combination with fructooligosaccharides, galactooligosaccharides, or sialyllactose individually. It may be seen that moderate protection was achieved using *L. rhamnosus* in combination with sialyllactose, but only at 10 g/l and not at 1 g/l as with the preparation of the invention.

Example 5

In vivo experiments were performed to compare the effects on the intestinal microbiota of supplementation with the prebiotic mixture alone, with a probiotic *Bifidobacterium lactis* alone and with a preparation according to the invention in a gnotobiotic animal model of human infant microbiota.

Germ free mice were gavaged with a model of human infant microbiota and the microbiota was allowed to establish itself for two weeks. The mice were then divided into four groups:—a first group who received 3% by weight of the prebiotic mixture alone in their food, a second group who received *Bifidobacterium lactis* CNCM I-3446 (NCC 2818) in their drinking water, a third group who received both the prebiotic-supplemented food and the probiotic supplemented water and a fourth control group. The faecal microbiota was monitored during the course of the study (two weeks) at the end of which period the animals were sacrificed and the small intestine microbiota was also investigated.

The results are shown in FIGS. 3, 4 and 5. From these Figures, it may be seen that a bifidogenic intestinal microbiota, as evidenced by the *Bifidobacterium breve* counts in the small intestine (FIG. 3) and decreased *Staphylococci* and *Clostridium perfringens* counts in faeces (FIGS. 4 and 5) is synergistically promoted by the preparation according to the invention compared to its individual components.

Example 6

In vivo experiments were performed to compare the effects on establishment and metabolic activity of *Bifidobacterium longum* in the gastrointestinal tract of germ free mice of supplementation with the prebiotic mixture alone, with a probiotic *Lactobacillus rhamnosus* strain alone and with a preparation according to the invention.

Germ free mice were gavaged with a model of human infant microbiota and microbiota establishment was monitored over time by plate counting and by evaluation of 16S rRNA levels indicating metabolic activity. 16S rRNA was amplified by polymerase chain reaction, products were separated on a denaturing gradient gel and quantified relative the constant 16S rRNA levels of *E. coli* which served as internal standard. The following treatments were compared:—control diet and control drink (water); control diet supplemented with 3% of the prebiotic mixture and water; control diet and *Lactobacillus rhamnosus* CGMCC 1.3724 (NCC 4007) in the drinking water; control diet supplemented with 3% of the prebiotic mixture and *Lactobacillus rhamnosus* CGMCC 1.3724 in the drinking water.

The results are shown in FIG. 6. The preparation according to the invention synergistically boosted general metabolic activity of resident *Bifidobacterium longum* during establishment of a human infant microbiota in germ free mice. Human baby microbiota resident *B. longum* counts were at similar levels after 14 days in the control group and the groups receiving the probiotic and the prebiotic mixture alone whereas relative metabolic activity was synergistically and significantly increased in the group given the preparation according to the invention (FIG. 6D as compared to 6A, B, C).

The invention claimed is:

1. A preparation comprising:
   a probiotic bacterial strain; and
   a prebiotic mixture comprising
   5-70 wt % of at least one N-acetylated oligosaccharide selected from the group consisting of GalNAcα1-3Galβ1-4Glc, Galβ1-6GalNacα1-3Galβ1-4Glc and combinations thereof,
   20-90 wt % of at least one neutral oligosaccharide selected from the group consisting of Galβ1-6Gal, Galβ1-6Galβ1-4Glc, Galβ1-6Galβ1-6Glc, Galβ1-3Galβ1-3Glc, Galβ1-3Galβ1-4Glc, Galβ1-6Galβ1-6Galβ1-4Glc, Galβ1-6Galβ1-3Galβ1-4Glc, Galβ1-3Galβ1-6Galβ1-4Glc, Galβ1-3Galβ1-3Galβ1-4Glc and combinations thereof, and
   5-50 wt % of at least one sialylated oligosaccharide selected from the group comprising consisting of NeuAcα2-3Galβ1-4Glc, NeuAcα2-6Galβ1-4Glc and combinations thereof.

2. The preparation of claim 1, wherein the prebiotic mixture comprises 15-40 wt % of the N-acetylated oligosaccharides, 40-60 wt % of the neutral oligosaccharides and 15-30 wt % of the sialylated oligosaccharides.

3. The preparation of claim 1, wherein the oligosaccharide mixture comprises 30 wt % of the N-acetylated oligosaccharides, 50 wt % of the neutral oligosaccharides and 20 wt % of the sialylated oligosaccharides.

4. The preparation of claim 1, wherein the oligosaccharide mixture comprises 10-70 wt % of the N-acetylated oligosaccharides, 20-80 wt % of the neutral oligosaccharides and 10-50 wt % of the sialylated oligosaccharides.

5. The preparation of claim 1, wherein the probiotic bacterial strain is a *Lactobacillus* strain.

6. The preparation of claim 5, wherein the *Lactobacillus* strain is selected from the group consisting of a *Lactobacillus rhamnosus*, a *Lactobacillus paracasei* and a *Lactobacillus reuteri*.

7. The preparation of claim 5, wherein the *Lactobacillus* strain is *Lactobacillus rhamnosus* CGMCC 1.3724.

8. The preparation of claim 5, wherein the *Lactobacillus* train is *Lactobacillus paracasei* CNCM I-2116.

9. The preparation of claim 1, wherein the probiotic bacterial strain is a *Bifidobacterium* strain.

10. The preparation of claim 9, wherein the *Bifidobacterium* strain is selected from the group consisting of a *Bifidobacterium lactis*, a *Bifidobacterium longum* and a *Bifidobacterium breve*.

11. The preparation of claim 9, wherein the *Bifidobacterium* strain is *Bifidobacterium longum* ATCC BAA-999.

12. The preparation of claim 1, wherein the probiotic bacteria is present in an amount from $10^2$ to $10^{10}$ cfu per gram of the prebiotic mixture.

13. A food product comprising a nutritional composition and a probiotic bacterial strain and a prebiotic mixture comprising 5-70 wt % of at least one N-acetylated oligosaccharide selected from the group consisting of GalNAcα1,3Galβ1,4Glc and Galβ1,6GalNacα1,3Galβ1,4Glc, 4Glc, 20-90 wt % of at least one neutral oligosaccharide selected from the group consisting of Galβ1,6Gal, Galβ1,6Galβ1, 4Glc Galβ1,6Galβ1,6Glc, Galβ1,3Galβ1,3Glc, Galβ1, 3Galβ1,4Glc, Galβ1,6Galβ1,6Galβ1,4Glc, Galβ1, 6Galβ1,3Galβ1,4Glc Galβ1,3Galβ1,4Glc, and Galβ1, 3Galβ1,3Galβ1,4Glc and 5-50 wt % of at least one sialylated oligosaccharide selected from the group consisting of NeuAcα2,3Galβ1,4Glc and NeuAcα2,6Galβ1,4Glc.

14. The food product as claimed in claim 13 which is an infant formula.

15. The food product as claimed in claim 13 which comprises 0.3 to 4% by weight, the probiotic bacterial strain and the prebiotic mixture, based on dry matter of the preparation.

* * * * *